United States Patent [19]
Källstrand et al.

[11] Patent Number: 5,660,169
[45] Date of Patent: Aug. 26, 1997

[54] DISPOSABLE INHALER WITH PULL-OFF SEAL

[75] Inventors: Göran Anders Vilhelm Källstrand, Bjärred; Per-Gunnar Nilsson, Malmö, both of Sweden

[73] Assignee: Astra Aktiebolag, Sodertalje, Sweden

[21] Appl. No.: 422,004

[22] Filed: Apr. 12, 1995

Related U.S. Application Data

[63] Continuation of Ser. No. 984,424, filed as PCT/SE91/00601 Sep. 10, 1991, abandoned.

[30] Foreign Application Priority Data

Sep. 12, 1990 [SE] Sweden ................. 9002895

[51] Int. Cl.⁶ ............... A61M 15/00; A61M 16/00; B05D 7/14; B65D 83/06
[52] U.S. Cl. ............... 128/203.15; 128/203.21
[58] Field of Search ........... 128/203.15, 203.21, 128/203.12, 203.13, 204.11, 203.23, 203.14; 206/528, 363, 530, 532, 534.1, 534.2, 538, 539; 220/23.4

[56] References Cited

U.S. PATENT DOCUMENTS

| | | | |
|---|---|---|---|
| 2,549,303 | 4/1951 | Friday | 128/203.21 |
| 4,265,236 | 5/1981 | Pacella | 128/203.13 |
| 4,811,731 | 3/1989 | Newell et al. | 128/203.15 |
| 4,817,800 | 4/1989 | Williams et al. | 128/203.15 |
| 4,841,964 | 6/1989 | Hurka et al. | 128/203.15 |
| 5,035,237 | 7/1991 | Newell et al. | 128/203.21 |
| 5,042,472 | 8/1991 | Bunin | 128/203.15 |
| 5,239,991 | 8/1993 | Chawla et al. | 128/203.15 |

FOREIGN PATENT DOCUMENTS

| | | | |
|---|---|---|---|
| 0404454 | 12/1990 | European Pat. Off. | 128/203.15 |
| 8901348 | 2/1989 | WIPO | 128/203.15 |

*Primary Examiner*—Kimberly L. Asher
*Attorney, Agent, or Firm*—White & Case

[57] ABSTRACT

The invention relates to a disposable breath-actuated inhaler comprising a housing forming an air flow path open at both ends, wherein one end forms an air inlet and one end forms an air outlet. The housing includes a compartment for storing a pharmaceutical powder to be inhaled which is located close to the air inlet and covered by a thin foil which seals the compartment in an airtight way. The foil can be removed from the compartment from outside the housing. Additionally, the housing has a constriction adjacent the powder compartment such that a turbulent air stream will be obtained at the constriction upon inhalation which will lift the powder out from the compartment and mix the powder into the air stream.

11 Claims, 3 Drawing Sheets

DISPOSABLE INHALER WITH PULL-OFF SEAL

This application is a continuation of application Ser. No. 07/984,424, filed as PCT/SE91/00601 Sep. 10, 1991, now abandoned.

TECHNICAL FIELD OF THE INVENTION

The present invention relates to a breath-actuated disposable inhaler of the kind having a generally tubular shape having two ends, one end forming an air inlet and one end forming an air outlet, the inhaler containing a pharmaceutical powder comprising particles of a respirable size which is to be inhaled.

BACKGROUND OF THE INVENTION

Disposable, breath-actuated inhalers of the kind described above are for instance disclosed in WO 89/01348, U.S. Pat. No. 4,265,236 and EP-A-0404454.

EP-A-0404454 discloses a disposable, breath-actuated inhaler comprising a chamber for a pharmaceutical powder, said chamber being provided with an air inlet and with an air outlet. The air inlet and outlet are covered by a common cover. The powder is disposed loosely in said comparatively large chamber which means that the powder not necessarily will be located at that location at which the air flow is most efficient.

U.S. Pat. No. 4,265,236 discloses a tubular disposable, breath-actuated inhaler comprising a flexible tube, the ends of which normally being sealingly inserted into each other. This kind of seal will not necessarily be moisture-proof. There furthermore is a risk that some amount of the powder may fall out of the inhaler when the ends of the tube are pulled apart.

WO 89/01348, in the embodiment most of interest here, discloses a tubular, disposable inhaler which is sealed in both ends by means of twist-off caps. The pharmaceutical powder is loosely disposed in the inhaler and, as in the other inhalers described above, there is a risk that some powder is lost when the inhaler is opened.

The objects of the invention are to provide a disposable inhaler of the kind described above in which the dose of pharmaceutical powder can be determined accurately and in which the pharmaceutical powder can be stored hermetically sealed and moisture-proof. The dose delivered by different specimens of the same inhaler should generally be constant. The inhaler finally should be easy to prepare for use and easy to use as well as being easy and cheap to manufacture.

BRIEF DESCRIPTION OF THE INVENTIVE CONCEPT

The above objects are achieved in that the disposable inhaler is provided with the features set forth in the appended main claim. Advantageous embodiments are set forth in the dependent claims.

BRIEF DESCRIPTION OF THE APPENDED DRAWINGS

FIG. 1 shows a perspective view of an inhaler according to the invention,

FIG. 2 shows a perspective view of an inhaler according to FIG. 1 but showing the two main parts of the inhaler in an unassembled state, FIGS. 3A–3C show different stages in the opening of the powder compartment of the inhaler of FIG. 1, FIG. 4 shows an end view of the air inlet of the inhaler in FIG. 1, FIGS. 5–7 show different possible embodiments of the constriction adjacent the powder compartment.

DETAILED DESCRIPTION OF A PREFERRED EMBODIMENT OF THE INVENTION.

Figure 1:
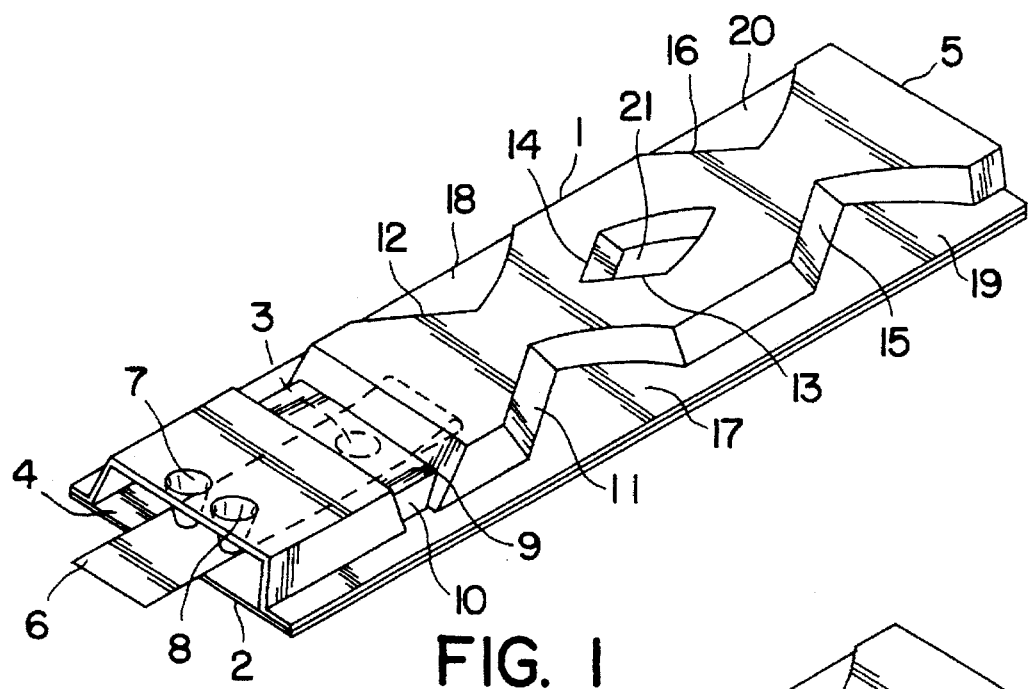

A preferred embodiment of the invention is disclosed in FIGS. 1–4. In FIG. 1 the inhaler can be seen in a fully assembled condition and ready for use. As can be seen, the inhaler essentially comprises two elongate main parts, an upper part 1 which is made of a moulded sheet of plastic material and a lower part 2 preferably made of aluminium foil laminated with plastic. The upper part 1 is U-shaped with a substantially rectangular shape. The width of the upper part is several times the height. The lower part is generally flat and the two parts thus form a tubular housing defining an air conduit or air flow path with an air inlet 4 and an air outlet 5. A part-spherical depression or recess 3 indicated with a dashed line is located close to the air inlet 4. The recess 3 forms a powder compartment and is covered by a tape 6 which preferably is made of aluminium foil, also laminated with plastic.

As indicated, the end of the part of the tape 6 covering the recess 3 is located between the recess 3 and the air inlet 4. The tape is attached to the lower part 2 around the powder compartment by means of a relatively weak weld 22 which can be seen in FIG. 2. The end of the tape is attached by a comparatively large and thus stronger weld in front of the compartment, as seen in the intended direction of the air flow. The free part of the tape 6 is bent backwards over the recess 3 and extends out through the air inlet 4. The free part of the tape is guided and held by two conical projections 7,8 extending downwards from the upper part 1.

A constriction in the flow path in the form of a ridge 9 oriented perpendicularly relative to the direction of the flow path is located above the powder compartment. The ridge is formed as a depression 9 in the upper part 1. The ridge is delimited at each end by an abutment 10.

The inhaler is further provided with deaggregation means after the powder compartment, as seen in the direction of the intended air flow through the inhaler. These deaggregation means comprise a number of oblique planar surfaces which are oriented at an angle of about 30° relative to the longitudinal direction of the inhaler, it surprisingly having been found that the most efficient angle of a planar surface relative to the air flow direction for disintegrating powder agglomerations is about 30°. Since the air flow will be deflected to some extent by the planar surface, the flow direction will not coincide fully with the longitudinal direction, but the above angle has been chosen as being the best compromise. The planar surfaces are oriented generally perpendicularly relative to the lower part 2, or at least as perpendicularly as the method of manufacturing the inhaler allows. The planar surfaces are located in such a way that their projections onto a cross-sectional plane substantially cover the entire cross-section of the inhaler. The projections preferably should overlap to some extent in order to ensure that any larger particles or agglomerations entrained in the air flow will impact on at least one such surface. In the preferred embodiment the planar surfaces 11, 12, 13, 14, 15, 16 are located on the upstream ends of two pairs of indentions 17, 18; 19, 20, formed into the sides of the upper part 1 and on the upstream end of a central depression 21 located between said indentations forming an island in the flow path. The downstream ends of said indentations and said depression taper in the direction of the air flow and have a smooth, rounded shape in order to obtain good aerodynamic conditions without any areas where the powder entrained in the air flow could settle.

Figure 2:
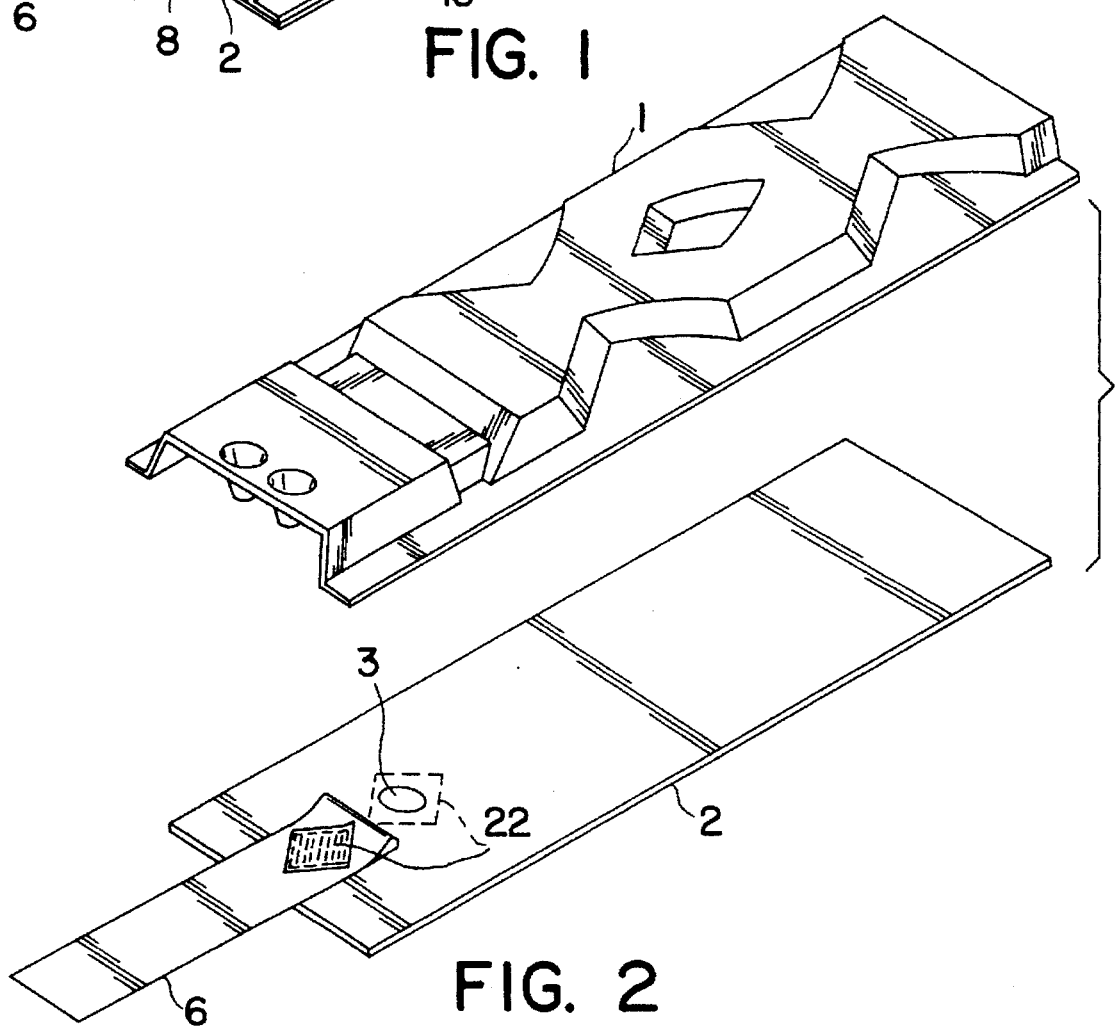

The two main parts of the inhaler are shown separated in FIG. 2. Apart from the details shown in FIG. 1, the powder compartment 3 is shown opened, the tape 6 having been pulled outwardly through the air inlet. The shape of the (broken) weld 22 can be seen on the tape 6 and around the powder compartment 3. As can be seen, the shape of the weld has been chosen to be the perimeter of a square oriented with one diagonal parallel with the longitudinal extent of the inhaler. This means that the disengagement of the tape from the lower part 2 will be facilitated since the tearing action will both start and end at a corner. Since the weld holding the inner end of the tape is broad and strong, the user will feel when the compartment has been uncovered by means of the increased resistance.

Figure 3A:
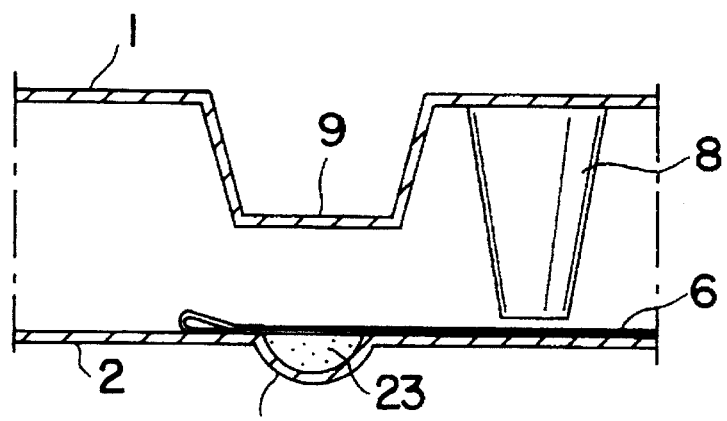
Figure 3B:
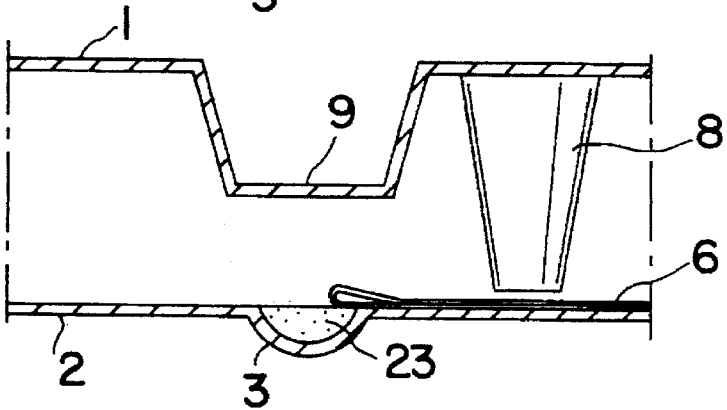
Figure 3C:
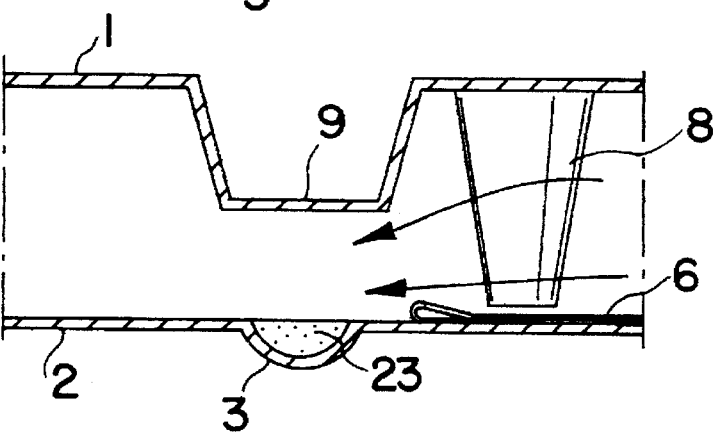

FIGS. 3A–3C show different stages in the opening of the powder compartment 3 by pulling the tape 6, thus exposing the powder 23.

Figure 4:
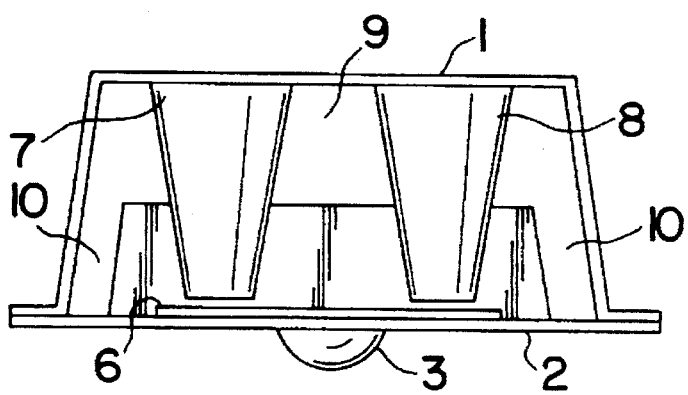
Figure 5:
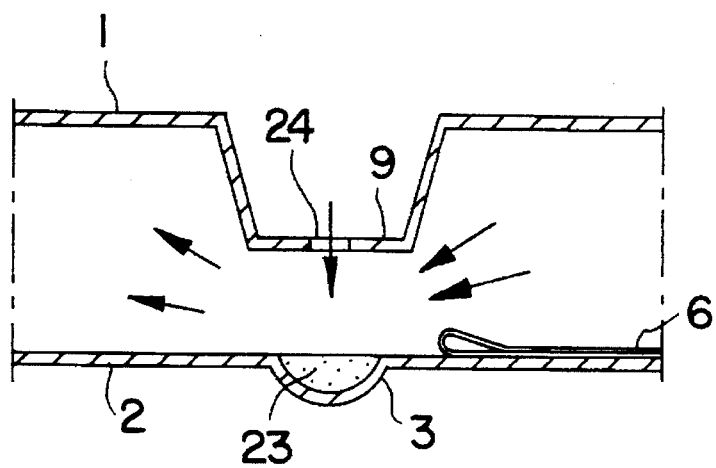
Figure 6:
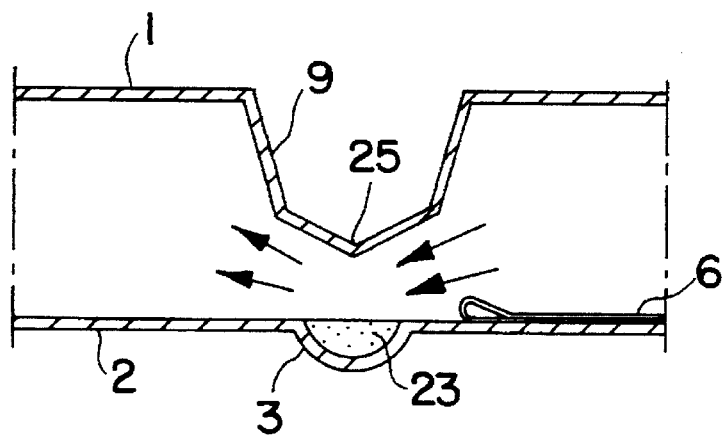
Figure 7:
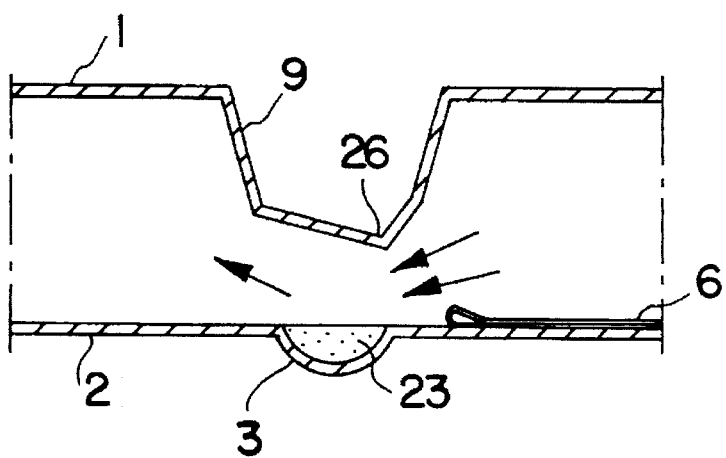

The end view in shown in FIG. 4 more clearly illustrates the inter-relationship between the upper part 1, the lower part 2, the powder compartment 3, the tape 6, the conical projections 7, 8, the ridge 9 and the abutments 10.

When the inhaler is to be used, the inhaler is held more or less horizontal with the flat half 2 facing downwards. The free end of the tape 6 is pulled outwardly and the powder in the powder compartment 3 is exposed. The two conical projections 7, 8 will hold the tape 6 flat against the lower part 2 and thus prevent the tape from occluding the constriction in front of the powder compartment. The user then inserts the air outlet into the mouth and inhales through the inhaler. The resultant air flow through the inhaler will become very turbulent in the region of the constriction and the pharmaceutical powder will be lifted out of the powder compartment and mixed with the air flow. Any particles adhering to the tape may also be entrained with the air flow since the part of the tape originally covering the powder compartment also will lie directly in the flow path.

Tests have shown that the dose leaving a typical powder compartment (about 0.5 mg) located at a constriction having an area of about 10–12 mm$^2$ will remain essentially constant at air flow rates varying from 30 l/min to 60 l/min.

The powder-laden air will then flow from the constriction to the deaggregation means. The angle of attack of the oblique surfaces will entail that the lighter particles, i.e. the particles within the respirable range, <6 μm, will be deflected from the surface without sticking thereto and thus mainly will follow the air flow, whereas the heaver particles and agglomerates will impact on and rebound from the planar surfaces and in this way be broken up into smaller particles. As mentioned above, an angle of about 30° may be optimal.

In this case tests again have shown that the percentage of particles within the respirable range in the dose to be inhaled will remain substantially constant at air flow rates ranging from 30 l/min to 60 l/min.

That the dose of respirable particles remains substantially constant over a wide range of air flows is important in order to minimize the difference between patients with different inhalation capacities.

It should be noted that the tubular shape of the inhaler makes it possible to mount a rubber ball or similar over the air inlet. By the means thereof the powder could be ejected from the inhaler into the throat of the patient in synchronization with the breathing of the patient by a helper if the patient should be incapable to use the inhaler by himself.

As mentioned above, the lower part 2 of the inhaler as well as the tape 6 preferably are made of aluminium foil laminated or coated with a suitable plastic. The aluminium will ensure the desired protection against moisture whereas the plastic will ensure that the tape can be welded to the lower part and that the lower part can be welded to the upper part. The lower part may for instance consist of a aluminium foil having a thickness of 45μ which on one side is covered with a layer of oriented polyamide which is 25μ thick and on the other side is covered by a layer of polypropene which is 60μ thick. The upper part is preferably made of polypropene being 300 or 400μ thick. The upper part can be transparent so that the user can see if the dose has been ejected from the powder compartment.

The tape may be made of a laminate having a "peel"-effect comprising polyester, aluminium and a layer comprising a polymer mixture of polybuten and polypropene.

The choice of material in the inhaler should be adapted to the drug to be used. The above materials have been chosen with a specific drug (budesonide) in mind, these materials releasing a dose of this drug more easily.

The composition of the pharmaceutical powder of course is quite optional and the powder may for instance comprise a pure active substance, a mixture of different active substances or a mixture of active substance(s) with adjuvant(s). It should be pointed out that the scope of choice of drugs is widened considerably due to the moisture-proof containment of the drug in the powder compartment.

The inhaler may be manufactured in the following way. A series of half-spherical indentations are formed in a strip of laminated aluminium foil in order to shape powder compartments. The indentations are filled with drugs and are topped off by means of scrapers, which will ensure a substantially uniform size of the different doses. An aluminium tape laminated with plastic is then welded over each indentation.

The lower parts are then welded to upper parts and the strip is cut to form individual inhalers which are ready for packaging and use. The upper parts are moulded from sheets of plastic. In the moulding procedure care should be taken to ensure that the side walls of the upper part are as perpendicular as possible relative to the upper side in order to ensure an air flow which is as uniform as possible throughout the entire cross-section of the inhaler. The function of the abutments 10 primarily are to prevent that the ridge forming the constriction is distorted during the welding process.

POSSIBLE MODIFICATIONS OF THE INVENTION

The invention of course can be modified in many ways within the scope of the appended claims.

Thus the ridge 9 forming the constriction can be designed in different ways in order to enhance the lifting action of the air flow on the powder. Some examples thereof can be found in FIGS. 5–7.

FIG. 5 illustrates how the ridge 9 can be provided with a small hole 24 centrally above the powder compartment 3. When the patient inhales through the inhaler, additional air will be directed more or less perpendicularly down into the powder compartment, thus enhancing the turbulent action in the vicinity of the powder compartment;

FIGS. 6 and. 7 illustrate two alternative embodiments wherein the ridge has been provided with an edge 25 resp 26 oriented along the longitudinal extent of the ridge and which also will direct some air flow more directly into the powder compartment.

These embodiments will however require a higher degree of precision in the manufacturing in order to obtain the desired effect than the embodiment described above and will therefore be more difficult to manufacture.

The ridge 9 forming the constriction has been illustrated as being generally trapezoid in cross-section and as being generally rectilinear in longitudinal section. It should however be pointed out that the constriction may be shaped in many different ways within the scope of the appended claims.

The powder compartment can of course have another shape than a half-spherical shape and may for instance be elliptical, the minor axis thereof being parallel with the direction of the air flow, or may be otherwise trough-shaped. It is of course also possible to have several indentations, for instance if it is desired to increase the dose in an exactly defined way.

The projections 7,8 can be shaped otherwise than conically and may for instance be shaped such that they direct a greater part of the air flow more directly past the powder compartment. They also could be integrated with the abutments 10.

The deaggregation means can be designed in other ways than in the form of planar surfaces oriented at an angle of about 30° relative to the direction of the air flow. This angle can be varied and the surface itself does not necessarily have to be planar.

The material in the lower part and the tape does not necessarily have to comprise aluminium and may be any plastic material having the necessary impermeability and stiffness or having been treated to have these properties.

It is also conceivable to make the inhaler from a single sheet which is rolled or folded after having been moulded in an appropriate way.

We claim:

1. A disposable breath-actuated inhaler comprising: a housing forming an air flow path being open at both ends, one end forming an air inlet and one end forming an air outlet, said housing further comprising a compartment for storing a pharmaceutical powder to be inhaled, wherein the compartment is located close to the air inlet and communicates with the air flow path through a compartment outlet, wherein the compartment is sealed from the air flow path by a tape covering the compartment outlet, wherein the inner end of the tape is attached to a lower part of said housing between the air inlet and the compartment, the tape extending past and being attached to the edges of the compartment outlet by means of a relatively weak weld, the tape then being bent backward away from the air outlet so as to extend through the air inlet, said housing being shaped with a constriction of the air flow path at the compartment outlet such that a turbulent air stream will be obtained at the constriction upon inhalation which will lift the pharmaceutical powder out from the compartment, through the compartment outlet and mix the pharmaceutical powder into the turbulent air stream which exits the air outlet.

2. The inhaler according to claim 1, wherein said housing is formed of two main parts comprising: a molded upper part and a generally flat lower part having a recess extending below the lower part to form the compartment, said upper and lower parts being joined together along their longitudinal sides.

3. The inhaler according to claim 2, wherein the molded upper part is molded from a thin sheet of plastic.

4. The inhaler according to claim 3, wherein the constriction is formed as a depression in the upper side of the molded upper part, the constriction is oriented transversely relative to the longitudinal axis of said housing and the constriction is located above the compartment formed in the generally flat lower part of said housing.

5. The inhaler according to claims 2, 3 or 4, wherein the lower part is made of aluminum foil laminated with plastic.

6. The inhaler according to claim 1, wherein the thin foil is in the shape of a tape having one free end extending out through the air inlet, said tape being attached around the edges of the compartment by means of at least one relatively weak weld.

7. The inhaler according to claim 1, wherein the relatively weak weld forms a point facing downstream in order to facilitate an initiation of a tearing action along the relatively weak weld when the tape is to be pulled out through the air inlet in order to expose the powder.

8. The inhaler according to claim 1 or 7, further comprising at least one projection extending downward from the upper part of said housing positioned between the compartment and the air inlet for holding the tape against the lower part of said housing in order to prevent the tape from obstructing the air flow path.

9. The inhaler according to claim 1, 2, 3 or 4 further comprising a means for deaggregation located in the air flow path between the compartment and the air outlet.

10. The inhaler according to claim 9, wherein said means for deaggregation comprises a plurality of planar surfaces oriented obliquely relative to the longitudinal axis of said housing, said plurality of planar surfaces being disposed generally perpendicularly to the plane of the lower part of said housing, a projection of said plurality of planar surfaces onto a cross-section of the housing substantially covering said cross-section.

11. The inhaler according to claim 1, wherein the air inlet and the air outlet are positioned at opposite ends of the longitudinal axis of said housing.

* * * * *